US007982026B2

(12) United States Patent
Kim et al.

(10) Patent No.: US 7,982,026 B2
(45) Date of Patent: Jul. 19, 2011

(54) FRET PROBES FOR FLUORESCENT DETECTION OF THE ESPS GENE (75) Inventors: Hyong-Ha Kim, Daejeon (KR); Nam Woong Song, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 714 days.

(21) Appl. No.: 11/920,077

(22) PCT Filed: May 9, 2006

(86) PCT No.: PCT/KR2006/001728
§ 371 (c)(1),
(2), (4) Date: Nov. 8, 2007

(87) PCT Pub. No.: WO2006/121277
PCT Pub. Date: Nov. 16, 2006

(65) Prior Publication Data
US 2010/0062423 A1    Mar. 11, 2010

(30) Foreign Application Priority Data

May 9, 2005   (KR) .................. 10-2005-0038322
May 8, 2006   (KR) .................. 10-2006-0040966

(51) Int. Cl.
C07H 21/04    (2006.01)
C12Q 1/68     (2006.01)
C12P 19/34    (2006.01)

(52) U.S. Cl. ...... 536/24.31; 435/6; 435/91.2; 536/24.33

(58) Field of Classification Search ............... 536/24.31; 435/6, 91.2
See application file for complete search history.

(56) References Cited

U.S. PATENT DOCUMENTS 7,700,275 B2 *    4/2010   Lee .................................. 435/6
2005/0026164 A1 * 2/2005   Zhou ............................... 435/6

FOREIGN PATENT DOCUMENTS

KR    2003-0381930    4/2003
KR    2004-0012260    2/2004

OTHER PUBLICATIONS

Lowe et al., A computer program for selection of oligonucleotide primers for polymerase chain reactions. Nucleic Acids Research, vol. 18, No. 7, pp. 1757-1761, 1990.*
S. Sixou, et al., 'Intracellular oligonucleotide hybridization detected by fluorescence resonance energy transfer (FRET)' In: Nucleic Acids Research, 1994, vol. 22 (4), pp. 662-668.
I. Wang, et al., 'Spectroscopic characterization of fluorescein—and tetramethylrhodamine-labeled oligonucleotides and their complexes with a DNA template', In: Spectrochimical Acta Part A, 2004, vol. 60, pp. 2741-2750.
WO 2002/097132 A2 (The Secretary of State DSTL, GB) Dec. 5, 2002.
Korean International Search Report, dated Aug. 22, 2006 PCT International Search Report (Form PCT/ISA/210).

* cited by examiner

*Primary Examiner* — Prabha Chunduru (57) ABSTRACT

The present invention relates to a primer pair for the detection of a specific gene, and more particularly to a probe pair for the detection and analysis of an EPSPS (5-enolpyruvylshikimate-3-phosphate synthase) gene, in which primers complementary to the base sequences in the EPSPS gene are labeled with fluorophores acting as an energy donor and an energy acceptor, respectively. By introducing the inventive probe pair into cells, hybridizing the primers of the probe pair with the target gene and then analyzing the biological cells in a single cell unit using laser fluorescence measurement technique, cells containing the EPSPS gene of GMOs can be detected and the percentage of the GM cells in a cell mixture can also be quantified.

6 Claims, 5 Drawing Sheets

FRET PROBES FOR FLUORESCENT DETECTION OF THE ESPS GENE

CROSS-REFERENCE TO RELATED APPLICATIONS

This application claims the benefit of PCT International Application Number PCT/KR2006/1728 filed May 9, 2006 and Korean Patent Application Nos. 10-2005-38322 filed on May 9, 2005 and 10-2006-40966 filed May 8, 2006 in the Korean Intellectual Property Office, the disclosure of which is incorporated herein by reference in its entirety.

TECHNICAL FIELD

The present invention relates to reagents for the detection and analysis of a specific gene, and more particularly to fluorescent detection reagents which detect cells containing EPSPS (5-enolpyruvylshikimate-3-phosphate synthase) gene of the genetically modified (GM) soybean single cells using laser fluorescence measurement technique, and can also quantify the content of the target-containing cells within a cell mixture.

BACKGROUND ART

As the up-to-date development of scientific technology has recently been concentrated on the biotechnology field, the importance of the analytical technique in the biological field has been increasingly emphasized. However, due to the immense complexity of the vital phenomena, and because of the involvement of various biological molecules in the analyses of biological samples it is very difficult to develop techniques for precise measurement. For this reason, standard measurement technique in the biological field involves many difficult problems in the procedure of the development thereof and is not yet established internationally. Because an attempt to develop the standard measurement technology in the biological field by partially improving experimental methods or introducing high-priced equipment while maintaining the framework of the pre-existing biological measurement methods has limitations for improvement, it is necessary to develop techniques based on new measurement principles in order to establish reliable bioanalytical methods.

Existing analytical methods which identify the presence of a specific gene or protein include PCR (polymerase chain reaction) and ELISA (enzyme linked immuno-sorbent assay), but these methods are carried out on cell extracts or (partially) purified molecules, but not on whole cells. A technique which can determine the presence of a specific gene or protein within a single cell may provide improved accuracy compared to the pre-existing analytical methods.

Meanwhile, as interest in GM foods has recently been accentuated, there is a need for a reliable method for GM food analysis.

DISCLOSURE

Technical Problem

It is an object of the present invention to provide fluorescent detection reagents which can detect cells with EPSPS gene of the GM soybean by analyzing cells by single cell detection using laser fluorescence measurement technique and quantify the content of GM cells in the cell mixture.

Technical Solution

To achieve the above object, the present invention provides a fluorescent probe pair for the detection of the EPSPS gene, the probe pair consisting of a pair of primers, which satisfy the following conditions: (A) the 3'-end and the 5'-end, which are close to each other when hybridized with the EPSPS gene, are labeled with a fluorescent energy donor (hereinafter, referred to as the "donor") and a fluorescent energy acceptor (hereinafter, referred to as the "acceptor"), respectively; and (B) the energy donor and the energy acceptor, when hybridized with the EPSPS, are located within a distance at which the fluorescence resonance energy transfer (FRET) between them can occur.

More specifically, the primer pair preferably has sequences shown in Table 1 and may be made of a DNA, RNA or PNA (peptide nucleic acid) oligomer.

In the present invention, fluorophores labeled on the primer pair were FAM (5-carboxy fluorescein) for the donor and TAMRA (5-carboxytetramethylrhodamine) for the acceptor, but are not limited thereto. Any donor and acceptor pair may be used in the present invention as long as fluorescence energy can be transferred thereto by resonance.

In Examples of the present invention, PNA oligomers were labeled with fluorophores by conjugating active compounds (Invitrogen) to PNAs. Specifically, as the active compounds, 5-FAM, SE (5-carboxyfluorescein, succinimidyl ester) was used for the introduction of FAM, and TAMRA, SE (5-carboxytetramethylrhodamine, succinimidyl ester) was used for the introduction of TAMRA.

TABLE 1

| Name of detection reagents | Base sequences (5'-3') | Labeled fluorophores | Role of fluorophores | SEQ ID NO | Remarks |
|---|---|---|---|---|---|
| S1 | ATGAACTCCGGG | 3'-FAM | Donor | SEQ ID NO: 1 | Set 1 |
| S2 | TCGTGGCGATCA | 5'-TAMRA | Acceptor | SEQ ID NO: 2 | |
| S3 | ATCGTCCACCGT | 3'-FAM | Donor | SEQ ID NO: 3 | Set 2 |
| S4 | GGGTTTTCCGAC | 5'-TAMRA | Acceptor | SEQ ID NO: 4 | |
| S5 | TCTCGCCCTCAT | 3'-FAM | Donor | SEQ ID NO: 5 | Set 3 |
| S6 | ATCCACGCCATT | 5'-TAMRA | Acceptor | SEQ ID NO: 6 | |
| S7 | CGCTTTCCTTGA | 3'-FAM | Donor | SEQ ID NO: 7 | Set 4 |
| S8 | GAGTTCTTCCAG | 5'-TAMRA | Acceptor | SEQ ID NO: 8 | |

Figure 1:
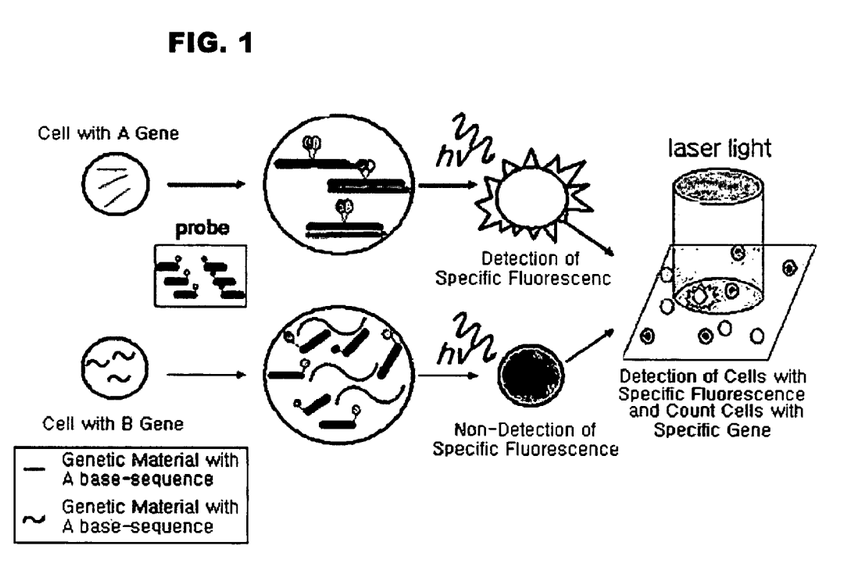
FIG. 1 is a schematic diagram showing the process of detecting cells with a specific gene among a mixture of cells using the FRET method.

FIG. 1 schematically shows that a cell containing the EPSPS gene can be detected using FRET fluorescence measurement for the specific probe pair according to the present invention. The FRET fluorescence measurement technique is based on Forster's theory that the resonance energy transfer efficiency between two fluorophores (donor and acceptor) is inversely proportional to the sixth power of the donor/acceptor distance. In order for the FRET fluorescence to occur, two fluorescent molecules must be located within a very short distance (less than 3-4 nm). When the probe pair according to the present invention does not bind to the EPSPS gene in aqueous solution or cells, the probe pair normally does not show FRET fluorescence, because the probability of the average distance between the donor and the acceptor to be coincidentally within the critical distance, and therefore FRET to occur, is low. On the contrary, if the probe pair binds to the EPSPS gene, the distance between the donor and the acceptor is set within a short distance. In this case, the fluorescence energy is transferred to the acceptor by donor excitation, and the specific fluorescence of the acceptor is observable.

In the probe pair, it is more preferable if the probe labeled with the acceptor is also labeled with a chromophore capable of quenching the acceptor fluorescence at the opposite end relative to the acceptor. In the present invention, the 3'-end of the probe labeled at the 5'-end with the acceptor TAMRA was covalently labeled with QSY-7 (Invitrogen) that quenches fluorescence. In order to introduce QSY-7 into the 3'-end of the PNA probe, QSY-7 succinimidyl ester was used.

Figure 2:
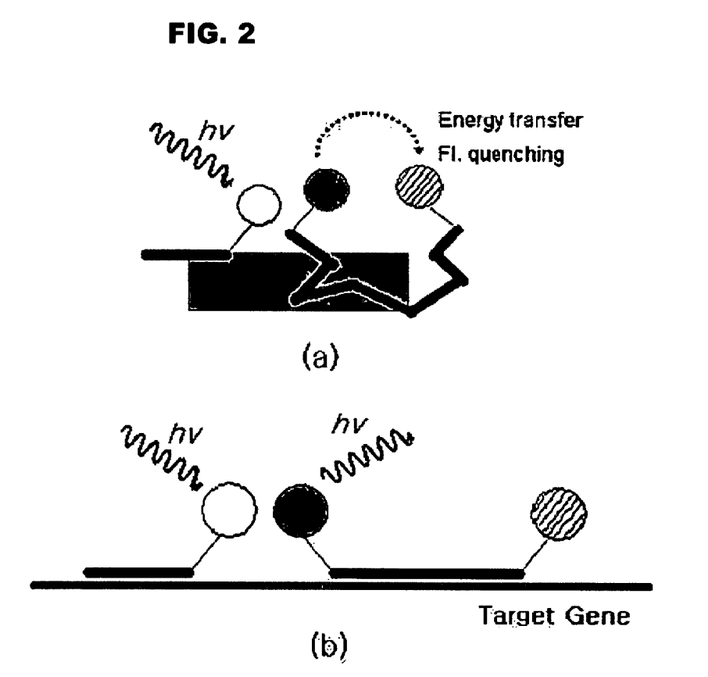
FIG. 2 is a schematic diagram showing a process of detecting a specific gene using an end-labeled acceptor probe with a fluorescent acceptor and a chromophore that quenches the fluorescence of the acceptor.

PNA, due to its hydrophobic molecular structure, prefers a hydrophobic environment and tends to shrink in aqueous solutions (H. Kuhn et al., J. Am. Chem. Soc. 2002, 124, 1097). As shown in FIG. 2(a), when the acceptor probe freely floats in an aqueous solution or is attached to biological molecules other than the EPSPS gene, PNA prefers a folded structure with both ends close together. The fluorescence emitted from TAMRA is mostly quenched by QSY-7 because of the close distance between TAMRA and QSY-7. Meanwhile, when the acceptor probe binds to the target gene, it obtains a straightened, linear molecular structure as shown in FIG. 2(b), which locates TAMRA and QSY-7 distant from each other, resulting in effective fluorescence emission. Meanwhile, when the acceptor probe binds to the target gene, it will have a straightened shape as shown in FIG. 2(b), and TAMRA and QSY-7 will be far away from each other, so that fluorescence will be effectively emitted. Thus, compared to an acceptor probe without QSY-7 labeling, in case of the quencher-containing probe structure, the amount of fluorescence emitted from the acceptor will greatly change depending on the state of the probe, i.e., free or bound to the target gene, because fluorescence emitted from the acceptor is quenched when the acceptor is not bound to the target gene. As described above, when the acceptor probe labeled with a quencher at the opposite end relative to the location of the acceptor is used for analysis, it is possible to obtain higher contrast in fluorescence while determining the presence or absence of the target gene in cells, thus increasing the efficiency of the target gene detection.

Figure 3:
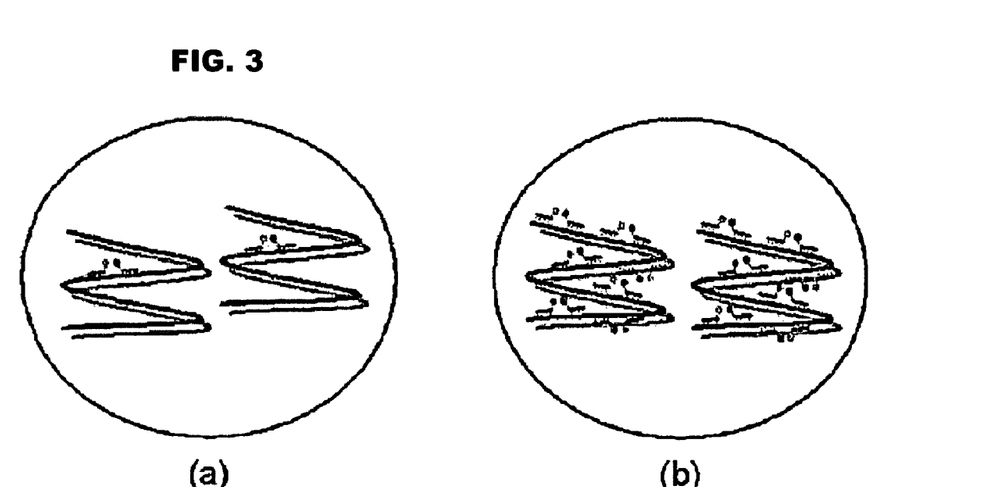
FIG. 3 is a schematic diagram showing the principle of amplifying signals using several different pairs of probes to detect the EPSPS gene in cells using the FRET method.

It is advantageous for target gene detection to use several different pairs of probes such that they can simultaneously bind to several different positions over the total length of the target gene (see FIG. 3). Particularly when the target gene is a single or a low-copy number gene, it is more preferable to use multiple pairs of probes. In fluorescent analysis of cells, natural fluorescent substances present in cells can increase the cellular background greatly. Fluorescence from a pair of specific probes binding to a single or a small number of molecules can be undetectable, because it can be a relatively weak signal compared to autofluorescence of the cell or other fluorescent substances within the cells (FIG. 3a). Several different pairs of probes which simultaneously bind to several different positions within the target gene can be introduced in cells to solve this problem. In this case, FRET fluorescence will simultaneously be emitted from several different positions and, as a result, the fluorescence intensity caused by the presence of the target gene will increase, making it easier to distinguish the positive signals from the natural fluorescence (FIG. 3b).

A process for the detection of the EPSPS gene in GM cells comprises the steps of: (A) introducing the inventive probe pair into cells and hybridizing the corresponding base sequences of a target gene with the primers of the probe pair; (B) determining the presence or absence of the EPSPS gene using a laser-induced fluorescence measurement method.

Hereinafter, each step of the process for detecting the EPSPS gene according to the present invention will be described in detail.

(A) Step of Introducing Probe Pair into Cells and Hybridizing it

For the analysis of the EPSPS gene-containing cells, this step is a step of introducing the inventive probe pair into cells and hybridizing the primers of the probe pair with the target gene. As described above, although a single pair of the probes can also be introduced into cells, it is more preferable to introduce at least two pairs of the probes into cells simultaneously and perform analysis in order to increase the background-to-noise fluorescence ratio of the target gene.

In the analysis of the EPSPS gene, because fluorophores (chlorophyll, etc.), which can be activated by external light, can exist in soybean cells, cells cultured for at least one week under light-shielded conditions are preferably used as analytical samples in order to minimize the fluorescence derived from the light-induced fluorophores.

As the method for introducing the probe pair into cells, any method selected from among chemical methods widely known in the art, methods using viral vectors, and physical methods, may be used. Because the introduction method does not correspond to the subject matter of the present invention, the detailed description thereof will be omitted herein. In Examples of the present invention, electroporation among the physical methods was used to introduce the probe pair into cells, but the present invention is not limited thereto. The said fluorescent detection reagents can be used in cell unit measurement, but it may, of cause, be used for in vitro detection.

(B) Step of Analysis by Fluorescence Measurement

This step is a step of using the principle of FRET fluorescence to analyze whether the EPSPS gene is present in the cell of the analytical sample.

When a pair of probes consist of a pair of primers with base sequences complementary to the flanking region in the EPSPS gene and labeled with donor and acceptor fluorophores, respectively, are introduced into cells, the probes do not show FRET fluorescence in cells with no EPSPS gene, because the pairs have no positional relationship therebetween within the cells so that the average distance between the donor and the acceptor is longer than the possible FRET distance. However, in cells containing the EPSPS gene, the probes labeled with the donor and the acceptor fluorophore will bind complementarily to the EPSPS gene and, at the same time, are within close enough distance so that FRET fluorescence can be emitted. Thus, the measurement of FRET fluorescence makes it possible to easily analyze whether the EPSPS gene is present in a cell of interest. Furthermore, through the use of this principle, the content of cells containing the EPSPS gene within a mixture of cells can be quantitatively analyzed.

In most cases, because the absorption of the acceptor in the wavelength of laser light for the donor excitation is not zero, not only an energy transfer from the donor, but also the direct absorption of the laser light by the acceptor itself, contributes to the acceptor fluorescence intensity resulting from laser excitation. For example, in test conditions of Example 1, since the acceptor fluorescence intensity is about 8-fold increased due to the transfer of energy from the donor, if the concentration of the acceptor in a solution for detection is unknown, it would be difficult to distinguish between a case where FRET occurred and another case where the acceptor concentration increased 8-fold. Particularly, if a donor and acceptor pair probe is introduced in cells for the detection of fluorescence, a more precise analytical attempt to normalize the background by measuring the concentration of the acceptor introduced in cells is required.

If target cells are irradiated with a specific laser light which can only excite the acceptor, the fluorescence intensity of the acceptor will be shown in proportion to the concentration of the acceptor introduced into cells, because the donor absorbs little or no laser light, and the acceptor exclusively absorbs laser light. Thus, by measuring the acceptor fluorescence intensity emitted while exciting the target cells with the exclusive absorption wavelength of the acceptor, it is possible to analyze the concentration of the acceptor reagent, which varies for each cell. When the degree of FRET fluorescence is normalized by dividing the acceptor fluorescence intensity obtained from donor excitation by the acceptor concentration value obtained using the result of the said analysis, it is possible to greatly reduce the signal ambiguities resulting from concentration differences of the fluorescent detection reagents introduced into cells.

ADVANTAGEOUS EFFECTS

The gene analysis method that employs the fluorescent detection reagents according to the present invention can be used to precisely measure the GM content within raw food material.

BEST MODE

Hereinafter, the present invention will be described in further detail with reference to examples. It is to be understood, however, that these examples are for illustrative purposes only and are not to be construed to limit the scope of the present invention. In the examples, although GM soybean was used for convenience, it is to be understood that any type of organism can be analyzed by detecting the EPSPS gene using the inventive probe pair and test method.

EXAMPLES

Example 1

Detection of EPSPS Gene in Solution Using FRET Measurement Technology

To examine the utility of the inventive analytical method, the presence or absence of DNA having the base sequence of herbicide-resistant gene EPSPS in GM plant Roundup Ready® (RR) soybean was determined in a buffered solution using the probe pair according to the present invention.

Figure 4:
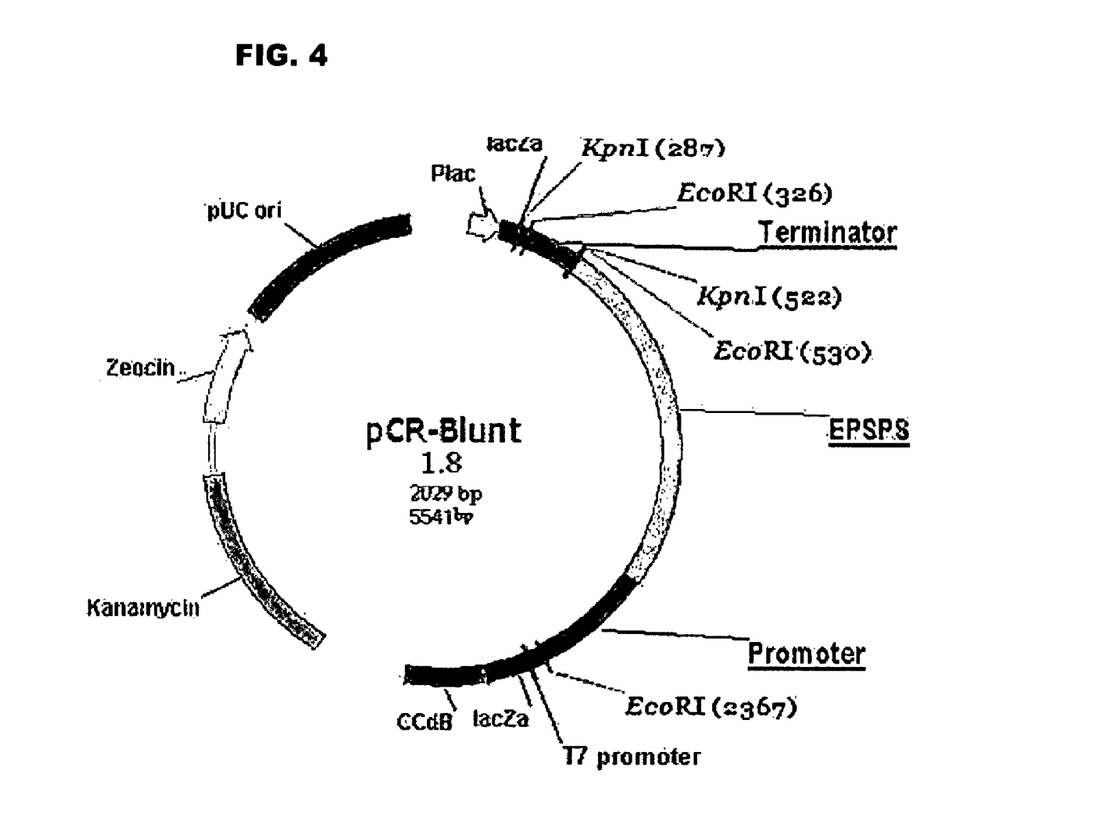
FIG. 4 is the map of plasmid pCRB-EPSPS1.8.
Figure 5:
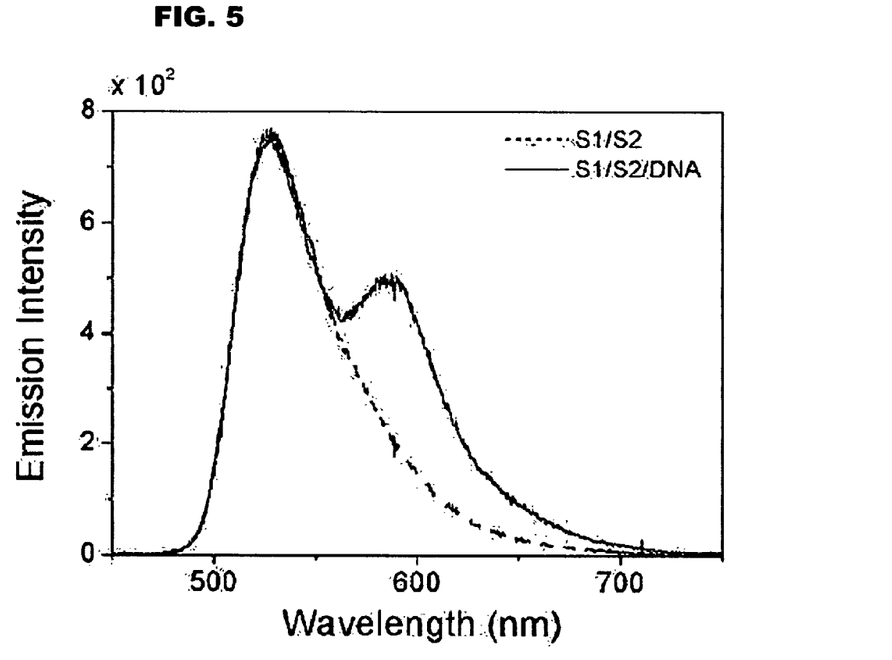
FIG. 5 is a typical spectrum pattern showing the detection of the EPSPS gene using an S1/S2 probe pair according to the present invention.
Figure 6:
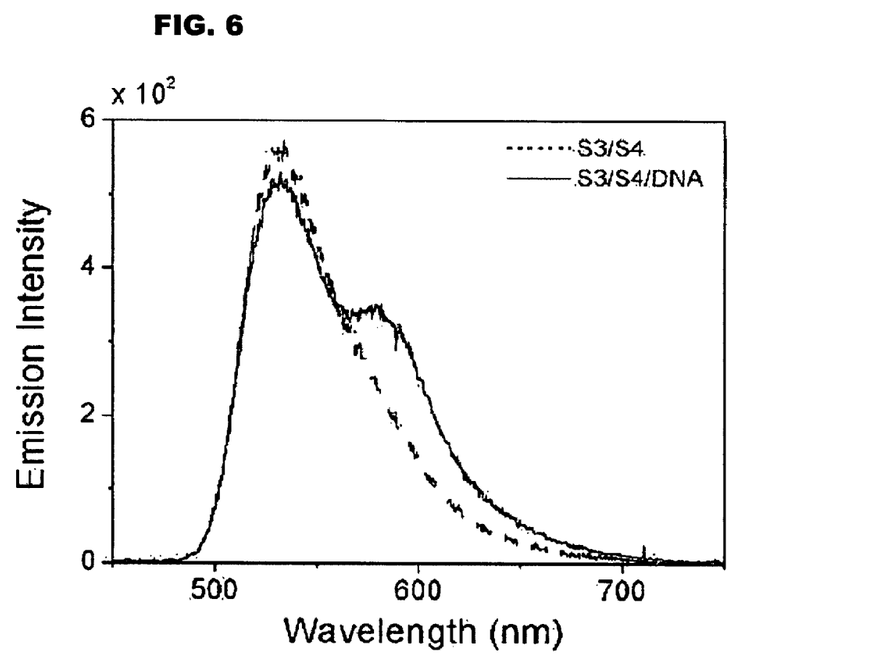
FIG. 6 is a typical spectrum pattern showing the detection of the EPSPS gene using an S3/S4 probe pair according to the present invention.
Figure 7:
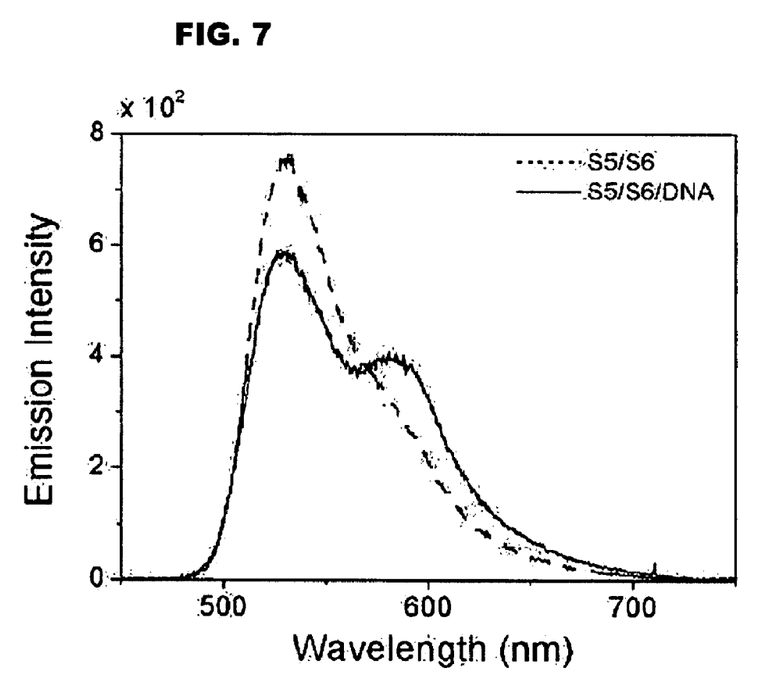
FIG. 7 is a typical spectrum pattern showing the detection of the EPSPS gene using an S5/S6 probe pair according to the present invention.
Figure 8:
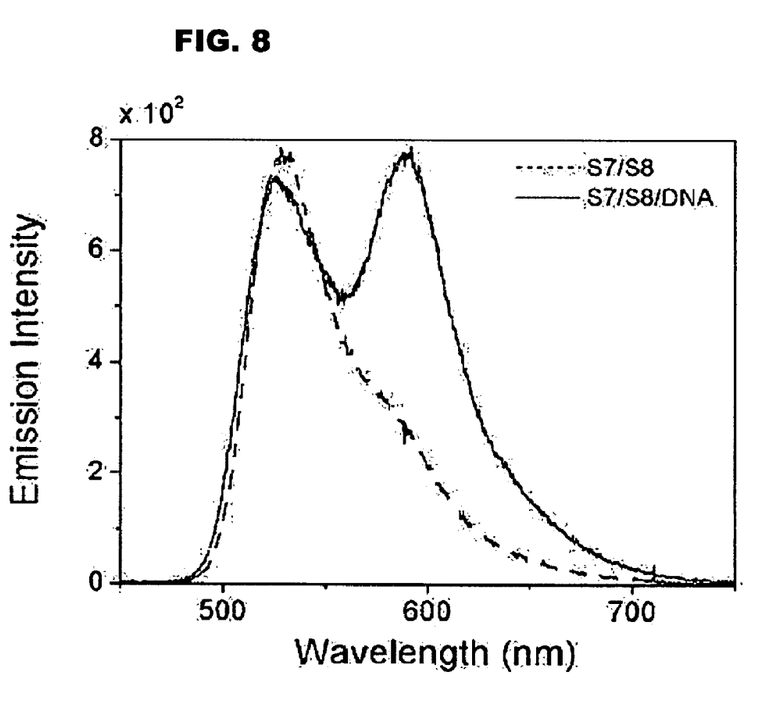
FIG. 8 is a typical spectrum pattern showing the detection of the EPSPS gene using an S7/S8 probe pair according to the present invention.

To ensure that the DNA containing the EPSPS sequence to be detected, the following steps were carried out. First, the genomic DNA of RR soybean, as a template, was amplified using PCR primers such that a region of about 2-kbp corresponding to the EPSPS gene, thus ensuring the amplified DNA having the EPSPS gene. As the PCR forward primer for amplification, 35S3F(5'-AAGATGCCTCTGCCGACA-3'; 18-mer; SEQ ID NO: 9) was used, and as the reverse primer, NOS3R(5'-ATGTATAATTGCGGGACTCTAATCA-3'; 25-mer; SEQ ID NO: 10) was used. The amplified DNA in this step was inserted into a DNA vector (pCR-blunt; 3.5 kb, Invitrogen, Carlsbad, Calif.), thus constructing a new plasmid (pCRB-EPSPS1.8; about 5.5 kbp) (see FIG. 4).

When the 2 kbp DNA corresponding to the EPSPS gene was required in larger amounts, the new plasmid DNA pCRB-EPSPS1.8 used as a template, was amplified by PCR using the same primers as described above. A total reaction mixture of 100 µℓ containing 3 µℓ DNA pCRB-EPSPS1.8 (10 ng/µℓ), 5 µℓ forward primer 35S3F (20 µM), 5 µℓ reverse primer NOS3R (100 µM), 10 µℓ dNTP (25 n04), 10 µℓ 10× buffer, 16 µℓ MgCl (25 mM), 0.8 µℓ Taq polymerase (5 U/µℓ) and distilled water to adjust reaction volume was added into one PCR tube. The PCR reaction was performed using gradient cycler PTC-0225 in the following PCR conditions: a denaturation step at 94° C. for 5 min; an amplification step of 35 cycles at 94° C. for 20 sec, 45° C. for 30 sec and 72° C. for 2 min; and a final elongation step at 72° C. for 10 min.

Each combination of the sets shown in Table 1 was used as a fluorescent detection reagent to generate FRET fluorescence by binding to the target gene. The primer region of the donor/acceptor probe pair was a PNA oligomer with a base sequence that could bind to the EPSPS DNA of RR soybean, and it was designed such that, when bound to the target gene, the donor and acceptor fluorophores were located close together while interposing four bases therebetween.

First, each of the following test tubes was prepared: a test tube in which only fluorescent detection reagents (donor concentration: 1 µM; acceptor concentration: 3 µM) were mixed at a volume ratio of donor:acceptor of 1:1; a test tube in which the target gene (concentration: 1,250 ng/ml) and the fluorescent detection reagents (donor concentration: 1 μM; acceptor concentration: 3 μM) were mixed at a volume ratio of DNA:donor:acceptor of 1:1:1.

Because of the double-helix DNA structure of the target gene in the solution, the fluorescent detection reagents may not easily bind to the target gene due to steric hindrance. In order to facilitate the binding between the target gene and the fluorescent detection reagents, the mixture solution was first heated to 95° C. for 3 minutes to denature the double-helix structure of the target gene. The temperature of the mixture solution was cooled to 45° C. at the rate of −6° C./min and incubated for 24 hours at 45° C., so the gene detection reagents could bind well to the desired positions of the target genes.

After 24 hours of incubation, the fluorescence spectrum of the solution was measured by exciting 442 nm laser light which mainly excites the donors. The donor has an absorption peak at 442 nm, whereas the acceptor has an absorption peak at 553 nm. Also, the donor fluorophore has little or no light absorption in a wavelength region longer than 530 nm, and the acceptor has very weak light absorption near 440 nm.

For the measurement of fluorescence spectrum, spectra in the wavelength region of 280-850 nm were simultaneously observed using a CCD light detector placed on the output end of a 150-mm focal-length spectrograph equipped with a grating of 300 gr/mm. For recording of the fluorescence spectrum, the sample solution was irradiated with laser light for 30 s, and two measurements of the emitted fluorescence signal was averaged.

As shown in FIGS. 5-8, in the solution containing no EPSPS DNA, it could be observed that the acceptor fluorescence appearing near 590 nm was weaker than the donor fluorescence appearing near 530 nm, however, in the solution containing the DNA, FRET fluorescence occurred due to the binding between the probes and the DNA, so that fluorescence near 590 nm remarkably increased.

This suggests that the target gene can be effectively detected in solution by FRET fluorescence measurement using the inventive probe pair. It was inferred that a specific gene can be detected effectively even in biological cells using this analytical method, because the detection of the target gene is carried out without removing the fluorophores after the reaction between the probes and the target gene.

This was confirmed through Example 2.

Example 2

Detection of EPSPS Gene in Biological Cells Using FRET Measurement Technique

1) Detection of EPSPS Gene Using Probe Pairs Labeled with FAM and TAMRA, Respectively The presence or absence of the EPSPS gene sequence could be determined for each single cell by measuring nonGM and GM RR soybean cells.

To detect the FRET fluorescence of nonGM soybean and EPSPS gene-containing GM RR soybean, the S7/S8 set was used in the test.

About $10^6$ cultured cells were added to 50 μℓ electroporation buffer (10 mM HEPES, 1 mM CaCl$_2$ solution), to which each of 50 μℓ of probes (donor concentration: 0.6 μM, acceptor concentration: 3 μM) was then added. Then, electroporation was performed once by applying an electric pulse of 220V, so that the donor and acceptor probes could be introduced into the cells. Then, the cells were incubated at 25° C. for 1 hour so that the primers of the probes could bind well to the desired positions of the target gene. After the cultured cells were immobilized on a cover glass, fluorescence spectra emitted from the individual cells were measured by alternately exciting the cells with 442 nm laser light of 20 μW and 514.5 nm laser light of 3 μW.

Figure 9:
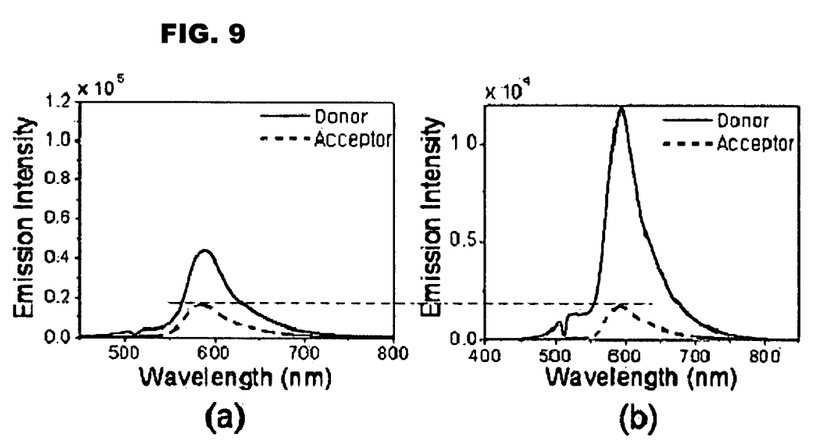
FIG. 9 is a typical spectrum pattern showing that (a) nonGM soybean cells and (b) GM soybean cells in which foreign gene EPSPS is present are distinguishable from each other using the S7/S8 probe pair according to the present invention.

As seen in FIG. 9, the nonGM soybean cells (a) and the GM RR soybean cells (b) were normalized for the different acceptor concentrations and then compared with each other with respect to FRET fluorescence. As a result, it could be observed that the cells containing the EPSPS target gene showed about 3-fold stronger fluorescence. This suggests that the method for determining the presence of the target gene by FRET fluorescence is a valid analytical method.

According to this principle, using a biological mixture separated into individual cell units, and by analyzing whether a target gene is present in each cell through the fluorescence of the detection reagents, the percentage of a specific cell among a mixed population can be measured by cell-counting.

2) Detection of EPSPS Gene Using FAM-Labeled Donor Probe and Acceptor Probe End-Labeled with TAMRA and QSY-7

Whether the presence or absence of the EPSPS gene sequence could be determined for each single cell was tested on nonGM soybean cells and GM RR soybean cells using improved probes with a more advantageous structure for the detection of the target gene in cells.

For the detection of FRET fluorescence of nonGM soybean and EPSPS gene-containing RR soybean, the S7/S8' set was used in the test. Herein, S7 is a donor with a structure shown in Table 1, and S8' is an acceptor with an improved structure in which PNA having the base sequence shown in Table 1 is labeled with TAMRA at the 5'-end and QSY-7 at the 3'-end.

About $10^6$ cultured cells were added to 200 μℓ of electroporation buffer (10 mM HEPES, 1 mM CaCl$_2$ solution), to which each of 50 μℓ of probes (donor concentration: 3 μM, acceptor concentration: 6 μM) was then added. Then, electroporation was performed once by applying an electric pulse of 220V, so that the donor and acceptor probes could be introduced into the cells. Then, the cells were incubated at 25° C. for 1 hour so that the primers of the probes could bind well to the desired positions of the target gene. After the cultured cells were immobilized on a cover glass, fluorescence spectra emitted from the individual cells were measured by alternately exciting the cells with 442 nm laser light of 10 μW and 543 nm laser light of 5 μW. A typical example of fluorescence spectra measured for the GM cell is shown in FIG. 10(a).

Figure 10:
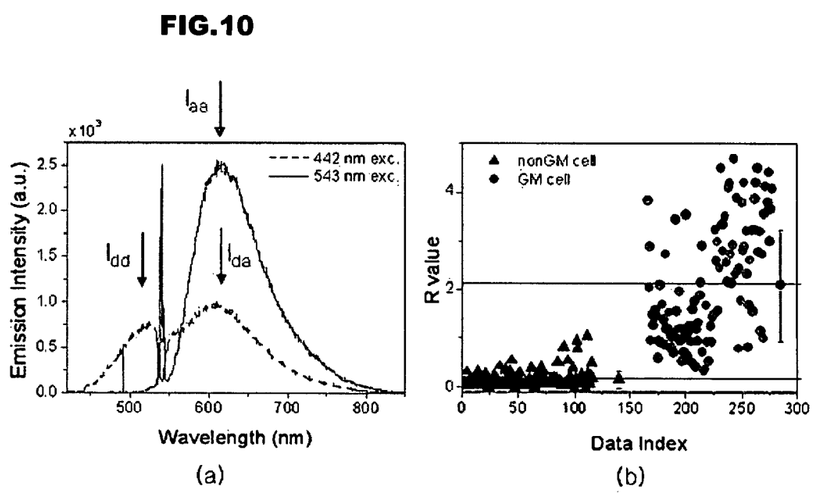
FIG. 10 is a typical spectrum pattern showing the detection of the EPSPS gene in a cell population and shows typical positive FRET fluorescence ratio.

FIG. 10(a) shows a fluorescence spectrum obtained by exciting a single GM cell with 442 nm laser light and 543 nm laser light, respectively. In order to determine the presence of the EPSPS gene in cells from the obtained fluorescence spectrum of a single cell, it is necessary to calculate FRET fluorescence ratio defined below in Equation 1 using fluorescence intensities measured at specific wavelength ranges.

$$R = I_{da}/I_{dd} \times I_{ad}/I_{dd} \quad (1)$$

wherein each of the fluorescence intensities is shown in FIG. 10(a), $I_{dd}$ represents the fluorescence intensity obtained from 442 nm excitation/520±30 nm detection, $I_{da}$ represents the fluorescence intensity obtained from 442 nm excitation/610±30 nm detection, and $I_{aa}$ represents the fluorescence intensity obtained from 543 nm excitation/610±30 nm detection. When FRET occurs, the donor fluorescence decreases and the acceptor fluorescence increases. Thus, the first factor $I_{da}/I_{dd}$ in Equation 1 is a parameter introduced to calculate values proportional to the change of the fluorescence intensity ratio. Also, as the acceptor binds to the EPSPS gene, the quenching of the acceptor diminishes and the fluorescence intensity of the acceptor increases. Thus, the second factor $I_{ad}/I_{dd}$ is a parameter introduced to calculate values proportional to this tendency. In addition, the concentration of the fluorescent detection reagents introduced into cells was normalized by dividing the fluorescence intensity of the acceptor by the fluorescence intensity of the donor.

Using this Equation, the laser-excited fluorescence spectrum of a single cell was measured on 110 GM cells and nonGM cells. Based on the obtained results, the R value was calculated for each cell using Equation (1). The R value measured for each cell is shown in FIG. 10(b). As shown in FIG. 10(b), the R values observed for the GM cells containing the EPSPS gene showed a distribution different from the R values observed for the nonGM cells with no EPSPS genes. The average of the R values for the GM cell group was 12 times higher when compared with the nonGM cell group. Reliabilities determined based on the R values at the single-cell level were 95.5% for the GM cells and 94.9% for the nonGM cells. These results suggest that the percentage of cells with a specific base sequence in a mixture of cells, which can be divided according to the base sequence of a gene, can be quantified with a reliability of about 95%.

INDUSTRIAL APPLICABILITY

The gene-based analysis method that employs the fluorescent detection reagents according to the present invention can be used to precisely determine the GM content within a given raw food material. According to the present invention, a raw food material is separated into individual cells, and then whether the cell contains a recombinant gene is examined on a high number (e.g., more than 10,000) of separated cells. Thus, the percentage of the GM cells can be quantified by counting the number of the cells containing the recombinant gene.

What is claimed is:

1. A probe pair for detecting an EPSPS gene, comprising: a pair of primers consisting of a first primer having a 3'-end, and a second primer having a 5'-end, wherein the first primer is labeled with an energy donor at the 3'-end, and the second primer is labeled with an energy acceptor at the 5'-end, which primers satisfy the following conditions when the probe pair is hybridized with the EPSPS gene:

the 3'-end of the first primer and the 5'-end of the second primer are close to each other when hybridized with the EPSPS gene; and the energy donor and the energy acceptor, when hybridized with the EPSPS gene, are located within a distance at which fluorescence resonance energy transfer (FRET) between them can occur, wherein the pair of primers is SEQ ID NO: 7 and SEQ ID NO:8.

2. The probe pair of claim 1, wherein an end of the second primer opposite the 5'-end is labeled with a chromophore that can quench fluorescence of the energy acceptor.

3. The probe pair of claim 1, wherein the primer pair is made of either DNA, RNA or PNA oligomers.

4. The probe pair of claim 1, wherein the energy donor is FAM (5-carboxy fluorescein), and the energy acceptor is TAMRA (5-carboxytetramethylthodamine).

5. The probe pair of claim 2, wherein the energy donor is FAM (5-carboxy fluorescein), the energy acceptor is TAMRA (5-carboxytetramethylthodamine), and the chromophore capable of quenching the fluorescence of the energy acceptor is QSY-7.

6. The probe pair of claim 2, wherein the primer pair is made of either DNA, RNA or PNA oligomers.

* * * * *

SEQUENCE LISTING

```
<160> NUMBER OF SEQ ID NOS: 10

<210> SEQ ID NO 1
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 1
atgaactccg gg                                                          12

<210> SEQ ID NO 2
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 2
tcgtggcgat ca                                                          12

<210> SEQ ID NO 3
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 3
atcgtccacc gt                                                          12

<210> SEQ ID NO 4
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 4
gggttttccg ac                                                          12

<210> SEQ ID NO 5
<211> LENGTH: 12
<212> TYPE: DNA
<213> ORGANISM: Artificial Sequence
<220> FEATURE:
```

-continued

<223> OTHER INFORMATION: primer of FRET probe for EPSPS gene detection

<400> SEQUENCE: 5
tctcgccctc at                                                         12

<210> SEQ ID NO 6
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 6
atccacgcca tt                                                         12

<210> SEQ ID NO 7
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 7
cgctttcctt ga                                                         12

<210> SEQ ID NO 8
<211> LENGTH: 12
<212> TYPE: DNA
<213> ORGANISM: Artificial Sequence
<220> FEATURE:
<223> OTHER INFORMATION: primer of FRET probe for EPSPS gene detection

<400> SEQUENCE: 8
gagttcttcc ag                                                         12

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
aagatgcctc tgccgaca                                                   18

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
atgtataatt gcgggactct aatca                                           25